(12) United States Patent
Fraden

(10) Patent No.: US 7,938,783 B2
(45) Date of Patent: *May 10, 2011

(54) MEDICAL BODY CORE THERMOMETER

(75) Inventor: Jacob Fraden, La Jolla, CA (US)

(73) Assignee: Advanced Monitors Corporation, San Diego, CA (US)

(*) Notice: Subject to any disclaimer, the term of this patent is extended or adjusted under 35 U.S.C. 154(b) by 1752 days.

This patent is subject to a terminal disclaimer.

(21) Appl. No.: 10/870,654

(22) Filed: Jun. 18, 2004

(65) Prior Publication Data

US 2005/0043631 A1 Feb. 24, 2005

Related U.S. Application Data

(60) Provisional application No. 60/495,952, filed on Aug. 19, 2003.

(51) Int. Cl.
*A61B 5/00* (2006.01)

(52) U.S. Cl. ............................... 600/549

(58) Field of Classification Search ............ 600/549, 600/474; 374/163, 164, 166, 169; 606/31
See application file for complete search history.

(56) References Cited

U.S. PATENT DOCUMENTS

| | | |
|---|---|---|
| 3,570,312 A | 3/1971 | Kreith |
| 3,681,991 A | 8/1972 | Eberly, Jr. ............ 73/362 |
| 3,832,902 A | 9/1974 | Usami et al. |
| 3,872,726 A | 3/1975 | Kauffeld ............ 73/362 |
| 3,893,058 A | 7/1975 | Keith ............ 338/28 |
| 3,903,744 A | 9/1975 | Cone ............ 73/362 |
| 3,933,045 A | 1/1976 | Fox et al. ............ 73/359 |
| 3,935,744 A | 2/1976 | Beckman ............ 73/361 |
| 3,942,123 A | 3/1976 | Georgi ............ 328/1 |
| 3,946,613 A | 3/1976 | Silver ............ 73/362 |
| 3,949,609 A | 4/1976 | Hammerslag ............ 73/362 |
| 3,978,325 A | 8/1976 | Goldstein et al. ............ 235/151.3 |
| 4,009,615 A | 3/1977 | Ruhl ............ 73/362 |
| 4,022,063 A | 5/1977 | West et al. ............ 73/362 |
| 4,068,526 A | 1/1978 | Goldstein ............ 73/362 |
| 4,158,965 A | 6/1979 | Prosky ............ 73/362 |
| 4,161,880 A | 7/1979 | Prosky ............ 73/342 |
| 4,166,389 A | 9/1979 | Montren ............ 73/343 |
| 4,204,429 A | 5/1980 | Shimazaki et al. ............ 73/362 |
| 4,411,535 A | 10/1983 | Schwarzschild ............ 374/165 |

(Continued)

FOREIGN PATENT DOCUMENTS

DE 2913048 A1 10/1980

(Continued)

OTHER PUBLICATIONS

Jacob Fraden, Handbook of Modern Sensors, Physics, Designs, and Applications, pp. 256-258, 1992.

(Continued)

*Primary Examiner* — Max Hindenburg
*Assistant Examiner* — Fangemonique Smith
(74) *Attorney, Agent, or Firm* — Wood, Herron & Evans, LLP

(57) ABSTRACT

A medical thermometer with a miniature sensor that touches the patient's skin by a spring-loaded probe. The device computes a deep body temperature by using data of probe housing temperature and accounting for multiple responses of skin contact temperature sensor before and after touching the skin. A motion detector is employed to turn power on automatically.

23 Claims, 4 Drawing Sheets

U.S. PATENT DOCUMENTS

| | | | | |
|---|---|---|---|---|
| 4,439,290 A | 3/1984 | Marfurt et al. | | 204/149 |
| 4,444,517 A | 4/1984 | Murase | | 374/188 |
| 4,454,370 A | 6/1984 | Voznick | | 136/221 |
| 4,457,633 A | 7/1984 | Andrews | | 374/209 |
| 4,461,584 A | 7/1984 | Murase | | 374/188 |
| 4,464,067 A | 8/1984 | Hanaoka | | 374/170 |
| 4,487,208 A | 12/1984 | Kamens | | 128/736 |
| 4,503,862 A | 3/1985 | Baessler | | 128/736 |
| 4,536,851 A | 8/1985 | Germanton et al. | | 364/557 |
| 4,537,518 A | 8/1985 | Murase | | 374/188 |
| 4,539,994 A | 9/1985 | Baumbach et al. | | 128/635 |
| 4,541,734 A | 9/1985 | Ishizaka | | 374/169 |
| 4,549,819 A | 10/1985 | Muramoto et al. | | 374/178 |
| 4,572,365 A | 2/1986 | Bruno et al. | | 206/306 |
| 4,588,306 A | 5/1986 | Burger et al. | | 374/158 |
| 4,602,871 A | 7/1986 | Hanaoka | | 374/102 |
| 4,619,271 A | 10/1986 | Burger et al. | | 128/736 |
| 4,629,336 A | 12/1986 | Ishizaka | | 374/169 |
| 4,636,091 A | 1/1987 | Pompei et al. | | 374/124 |
| 4,648,055 A | 3/1987 | Ishizaka et al. | | 364/557 |
| 4,691,713 A | 9/1987 | Suzuki | | 128/736 |
| 4,729,672 A | 3/1988 | Takagi | | 374/208 |
| 4,763,522 A | 8/1988 | Pompei | | 73/338 |
| 4,790,324 A | 12/1988 | O'Hara et al. | | |
| 4,843,577 A | 6/1989 | Muramoto | | 364/557 |
| 4,846,583 A | 7/1989 | Yamamoto | | 374/163 |
| 4,854,730 A | 8/1989 | Fraden | | |
| 4,863,279 A | 9/1989 | Markel et al. | | 374/109 |
| 4,866,621 A | 9/1989 | Ono | | 364/413.03 |
| 4,874,253 A | 10/1989 | Pompei et al. | | 374/121 |
| 4,877,333 A | 10/1989 | Ota et al. | | 374/169 |
| 4,930,222 A | 6/1990 | Nakanishi et al. | | 374/170 |
| 4,987,579 A | 1/1991 | Yoshinaka et al. | | 377/25 |
| 4,993,419 A | 2/1991 | Pompei et al. | | 128/664 |
| 5,011,294 A | 4/1991 | Yamaguchi | | 374/107 |
| 5,012,813 A | 5/1991 | Pompei et al. | | 128/664 |
| 5,017,019 A | 5/1991 | Pompei | | 374/133 |
| 5,050,612 A | 9/1991 | Matsumura | | 128/670 |
| 5,056,048 A | 10/1991 | Seperant | | 364/557 |
| 5,088,836 A | 2/1992 | Yamada et al. | | 374/183 |
| 5,088,837 A | 2/1992 | Shiokawa et al. | | 374/185 |
| 5,116,136 A | 5/1992 | Newman et al. | | 374/102 |
| 5,126,937 A | 6/1992 | Yamaguchi et al. | | 364/413.11 |
| 5,149,200 A | 9/1992 | Shiokawa et al. | | 374/185 |
| 5,150,969 A | 9/1992 | Goldberg et al. | | 374/128 |
| 5,178,468 A | 1/1993 | Shiokawa et al. | | 374/185 |
| 5,183,337 A | 2/1993 | Pompei | | 374/2 |
| 5,199,436 A | 4/1993 | Pompei et al. | | 128/664 |
| 5,259,389 A | 11/1993 | Muramoto et al. | | 128/736 |
| 5,271,407 A | 12/1993 | Pompei et al. | | 128/664 |
| 5,295,746 A | 3/1994 | Friauf et al. | | 374/170 |
| 5,325,863 A | 7/1994 | Pompei | | 128/736 |
| 5,333,784 A | 8/1994 | Pompei | | 236/91 C |
| 5,381,796 A | 1/1995 | Pompei | | 128/664 |
| 5,445,158 A | 8/1995 | Pompei | | 128/664 |
| 5,469,855 A | 11/1995 | Pompei | | 128/664 |
| D370,860 S | 6/1996 | Pompei et al. | | D10/57 |
| 5,628,323 A | 5/1997 | Pompei | | 128/664 |
| 5,632,555 A | 5/1997 | Gregory et al. | | 374/102 |
| RE35,554 E | 7/1997 | Pompei | | 374/121 |
| 5,642,735 A | 7/1997 | Kolbly | | 128/736 |
| 5,653,238 A | 8/1997 | Pompei | | 128/664 |
| 5,653,239 A | 8/1997 | Pompei et al. | | 128/664 |
| 5,655,305 A | 8/1997 | Fletcher | | 374/170 |
| 5,688,266 A | 11/1997 | Edwards et al. | | 606/31 |
| 5,725,308 A | 3/1998 | Smith et al. | | 374/169 |
| 5,732,711 A | 3/1998 | Fitzpatrick et al. | | 128/736 |
| 5,743,648 A | 4/1998 | Zeindler | | 374/151 |
| 5,836,692 A | 11/1998 | Pompei | | 374/121 |
| 5,873,833 A | 2/1999 | Pompei | | 600/474 |
| 5,874,736 A | 2/1999 | Pompei | | 250/338.1 |
| 5,893,833 A | 4/1999 | Pompei et al. | | 600/549 |
| 5,894,126 A | 4/1999 | Pompei et al. | | 250/338.1 |
| 5,897,552 A | 4/1999 | Edwards et al. | | 606/31 |
| 6,000,846 A | 12/1999 | Gregory et al. | | 374/164 |
| 6,036,361 A | 3/2000 | Gregory et al. | | 374/185 |
| 6,045,257 A | 4/2000 | Pompei et al. | | 374/132 |
| 6,047,205 A | 4/2000 | Pompei | | 600/474 |
| 6,048,902 A | 4/2000 | Lebwohl et al. | | 514/725 |
| 6,056,435 A | 5/2000 | Pompei | | 374/133 |
| 6,059,452 A | 5/2000 | Smith et al. | | 374/169 |
| 6,068,399 A | 5/2000 | Tseng | | 374/163 |
| 6,074,090 A | 6/2000 | Chen | | 374/183 |
| 6,146,015 A | 11/2000 | Weiss | | 374/164 |
| 6,186,959 B1 * | 2/2001 | Canfield et al. | | 600/559 |
| 6,219,573 B1 | 4/2001 | Pompei | | 600/474 |
| 6,220,750 B1 | 4/2001 | Palti | | 374/164 |
| 6,241,384 B1 | 6/2001 | Pompei et al. | | 374/126 |
| 6,250,802 B1 | 6/2001 | Doton | | 374/164 |
| 6,257,758 B1 | 7/2001 | Culbertson | | 374/120 |
| 6,280,397 B1 | 8/2001 | Yarden et al. | | 600/549 |
| 6,292,685 B1 | 9/2001 | Pompei | | 600/474 |
| 6,299,347 B1 | 10/2001 | Pompei | | 374/133 |
| 6,319,206 B1 | 11/2001 | Pompei et al. | | 600/549 |
| 6,402,371 B2 | 6/2002 | Pompei et al. | | 374/128 |
| 6,419,388 B2 | 7/2002 | Lee | | 374/208 |
| 6,450,970 B1 | 9/2002 | Mahler et al. | | 600/549 |
| 6,499,877 B2 | 12/2002 | Pompei | | 374/133 |
| 6,522,912 B1 | 2/2003 | Nakatani et al. | | 600/474 |
| 6,547,744 B1 | 4/2003 | Pompei et al. | | 600/549 |
| 6,629,776 B2 | 10/2003 | Bell et al. | | 374/170 |
| 6,641,301 B2 | 11/2003 | Pompei | | 374/125 |
| 6,794,990 B2 | 9/2004 | Tseng | | 340/584 |
| 6,827,487 B2 | 12/2004 | Baumbach | | 374/164 |
| 6,830,549 B2 | 12/2004 | Bui et al. | | 600/549 |
| 6,839,651 B2 | 1/2005 | Lantz et al. | | 702/130 |
| 6,854,882 B2 | 2/2005 | Chen | | 374/208 |
| 2002/0150143 A1 * | 10/2002 | Tokita et al. | | 374/163 |
| 2004/0025871 A1 * | 2/2004 | Davies | | 128/203.12 |

FOREIGN PATENT DOCUMENTS

| | | |
|---|---|---|
| EP | 0747682 A1 | 12/1996 |
| WO | 96/19938 A1 | 7/1996 |

OTHER PUBLICATIONS

European Patent Office, Supplementary European Search Report in EP Application No. EP05713646, May 28, 2009.

* cited by examiner

MEDICAL BODY CORE THERMOMETER

FIELD OF INVENTION

This invention is based on U.S. Provisional Patent Application No. 60/495,952 filed on Aug. 19, 2003 and relates to medical thermometers. More particularly it relates to intermittent thermometers that display core body temperature.

DESCRIPTION OF PRIOR ART

Body temperature is universally accepted as an important indicator of the physical condition of humans and other warm blooded animals. For many years, the most common method of measuring body temperature was to insert a mercury-in glass thermometer into the patient's mouth or rectum. These thermometers are potentially hazardous because of a possibility of mercury spill and glass breakage. The closest alternative is an the electronic "pencil" thermometers. These traditional thermometers will not register a body temperature until after they are left in the patient's mouth, rectum or other location for several minutes, thus making the measurement slow and uncomfortable.

A more advanced instrumentation has been developed to measure human body temperature by non-contact readings of the infrared (IR) emissions from the tympanic membrane and the ear canal. This technology was the subject of many patents, including O'Hara et al. U.S. Pat. No. 4,790,324 and Fraden U.S. Pat. No. 4,854,730. The determination of body temperature from an IR reading of the ear drum or ear canal avoids a need to insert a probe into the mouth or anus and allows a measurement of body temperature within a few seconds. However, the IR thermometers have their own problem, the most important of which is susceptibility to operator's technique of taking a temperature. Other drawbacks include effects of ambient temperatures, sensitivity to the cleanliness of the IR lens, etc. The IR thermometers are also relatively expensive.

Another IR thermometer which is exemplified by U.S. publication No. 2002/0114375 by Pompei, describes estimation of a core temperature by measuring the skin temperature and the ambient temperature by use of an IR emission detector. This method, however, suffers from other limitations, such as inability to accurately measure ambient temperature adjacent to the skin, perspiration effects, influence of an operator's technique, higher cost and other factors.

Any traditional contact (non-IR) thermometer has a probe with a temperature sensor that responds to temperature of an object. The rate of response depends on the degree of a thermal coupling with the object, nature of an object, the sensor's isolation from other components and its thermal capacity. There are two known techniques in art of a contact thermometry. One is the equilibrium and the other is the predictive technique. The equilibrium demands a sufficiently long time to allow the sensor to stabilize it's response, meaning that the sensor's temperature and the object's temperature become nearly equal. The predictive technique is based on measuring rate of the sensor's response and estimation of its would be equilibrium level which is not actually achieved during the measurement but rather anticipated mathematically. The latter technique allows a much quicker measurement alas on the expense of some loss in accuracy. The predictive method is covered by numerous U.S. patents exemplified by U.S. Pat. No. 3,978,325. Some of the predictive techniques rely on a software data processing, while others—on a hardware design. For instance, U.S. Pat. No. 3,872,726 issued to Kauffeld et al. teaches forecasting the ultimate temperature of a slow responding thermistor in a contact thermometer by using a hardware integrator.

It is an object of the present invention to provide an electronic thermometer that can register a core body temperature of a mammal without being inserted in the mouth or rectum.

It is another object of the present invention to provide an electronic thermometer that can register a core (deep body) body temperature of a mammal within seconds of contacting the patient skin.

It is another object of the present invention to provide a thermometer that determines core body temperature that is less susceptible to the operator's technique.

Further and additional objects are apparent from the following discussion of the present invention and the preferred embodiment.

SUMMARY OF THE INVENTION

The intermittent contact hand-held medical thermometer contains a probe with at least one temperature sensors. If more than one sensor is used, these sensors are thermally separated from each other, and one of the sensors contacts the patient skin while the other is thermally separated from the skin. By measuring responses of both sensors, the patient's deep body (core) temperature is computed by the microcontroller that takes into account temperature of the sensor prior touching the skin, ambient temperature, thermal resistance between the two temperature sensors and other factors.

DESCRIPTION OF PREFERRED EMBODIMENT

Two major issues of a patient temperature measurement are solved by this invention. The first is the speed response and the second is measurement of the core temperature without penetrating the body surface. The thermometer is intended for the intermittent measurement of a patient temperature by touching a selected location on the patient's body.

Figure 1:
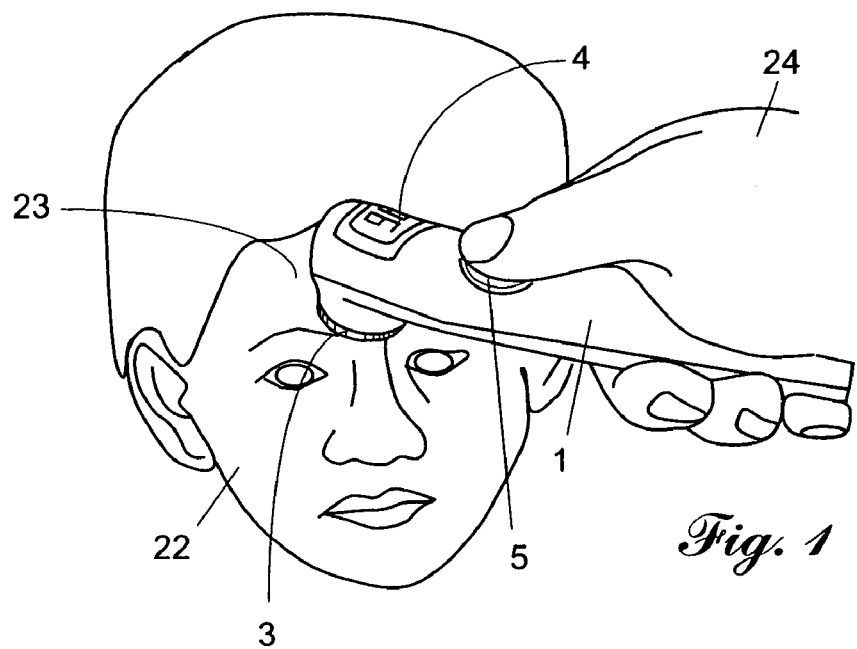
FIG. 1 is a representation of the thermometer whose probe touches skin of the patient's forehead.
Figure 3:
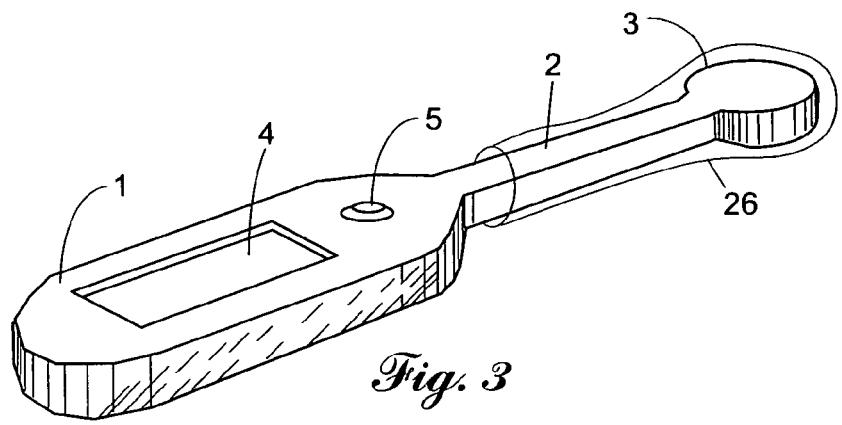
FIG. 3 shows a thermometer with the probe enveloped by a probe cover

Appearance of a basic device in operation is shown in FIG. 1. The device has housing 1 that is held by hand 24. Switch 5 can be used to power up the device and take a measurement. The result of measurement is represented on display 4. Probe 3 touches skin (for example, forehead 23) of patient 22. FIG. 3 shows another embodiment of the thermometer that contains elongated neck 2 and probe 3 which are enveloped by sanitary probe cover 26 that is of a conventional design.

Usually, the probe covers are narrow elongated bags fabricated of thin polymer film having thickness on the order of 0.001 inch.

Primarily, this thermometer is intended for the surface temperature measurements from such body sites as an a carotid artery region behind the ear lobe, armpit, chest, abdomen, groin, and forehead. Design of a practical probe will be influenced by a selected measurement site. The basic design principles outlined below are exemplified for a forehead probe and in most parts will be applicable for other body site probes.

Figure 2:
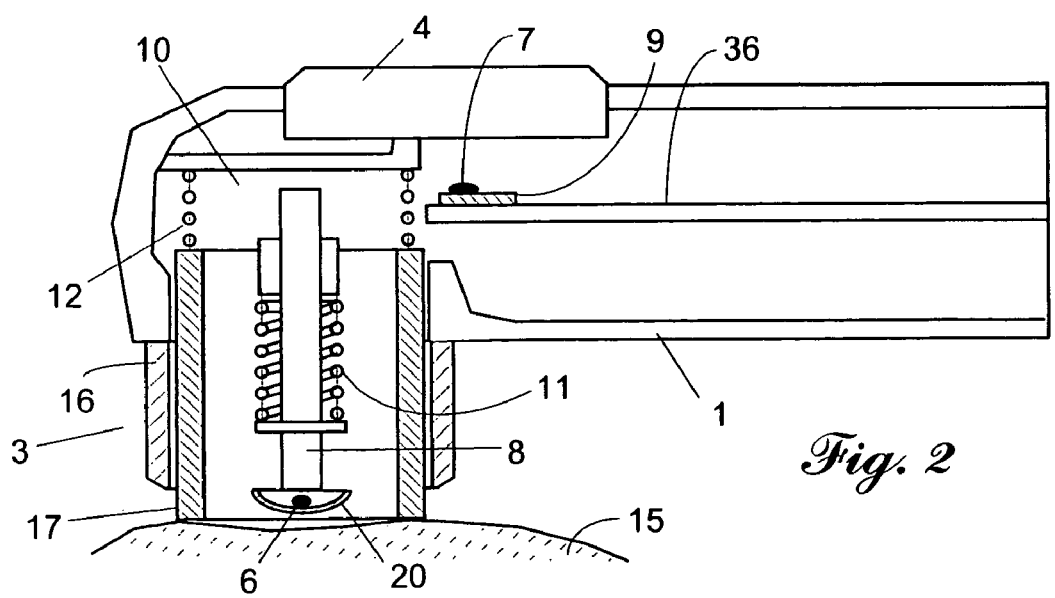
FIG. 2 is a cross-sectional representation of the probe with two absolute temperature sensors and a spring loaded thermal contact.

FIG. 2 shows a cross-sectional view of probe 3. It contains three essential components: first sensor 6, second sensor 7 and thermal insulator 10 which is positioned between the two sensors. The insulator may be fabricated of any conventional insulating material or it may be just void or air space between the two sensors. The sensors are the absolute temperature sensors such as thermistors, semiconductors or RTDs. Here word "absolute" means that they can measure temperature with reference to the absolute temperature scale. Naturally, other types of sensors can be employed, such as thermocouples. However, a thermocouple being a relative sensor would require use of an absolute reference sensor. Below, we use the absolute sensors to illustrate the operating principle. Sensor 6 is intended for coming into a thermal contact with the patient skin, while sensor 7 is thermally insulated from the patient at all times.

For stabilizing a thermal response, sensor 7 can be attached to thermal mass 9 that may be a metal plate. Thermal mass 9 may be supported by circuit board 36. Likewise, sensor 6 can be attached to plate 20 that is also fabricated of metal. It is important to provide a good thermal coupling between first sensor 6 and plate 20. To improve thermal contact with a patient, plate 20 may be made movable. It is supported by shaft 8 that is mechanically connected to first spring 11 and can move in and out of probe 3. The spring helps to assure a constant and reliable pressure applied by plate 20 to skin 15. Shaft 8 should be fabricate of a material with low thermal conductivity and preferably should be made hollow (see FIG. 8). Both sensors are connected to electronic components on circuit board 36 via conductors that are not shown in FIG. 2.

To protect a delicate probe tip (plate 20 and shaft 8) while handling or in storage, another movable component may be employed (FIG. 2). It is guard 17 that is pushed downward by second spring 12. Guard 17 can move in and out of sleeve 16. Guard 17 and sleeve 16 can be fabricated of plastic and should be positioned sufficiently outward of plate 20. When probe 3 is not touching skin 15, guard 17 is protruding from sleeve 16, thus shielding plate 20 from possible mechanical damages. When probe 3 comes in contacts with skin 15 and a sufficient pressure is applied, guard 17 slides inside sleeve 16, thus exposing plate 20 and allowing it to come in contact with skin 15. Further pressure compresses both springs 11 and 12 until guard 17 reaches its limit of movement. This provides a predetermined degree of first spring 11 compression and aids in consistency of measurements.

Figure 4:
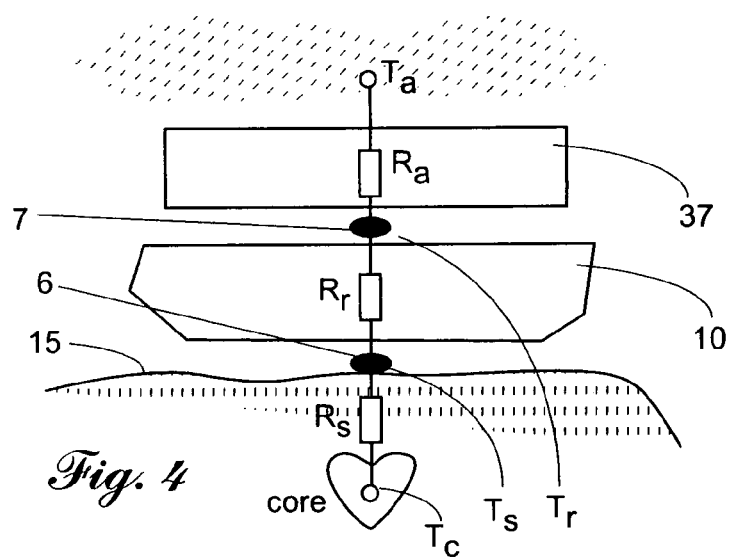
FIG. 4 is a thermal diagram of the sensor touching the skin

FIG. 4 illustrated the principle of measuring core temperature. When probe 3 is pressed against patient's skin 15, first temperature sensor 6 becomes thermally coupled to the patient core through the patient body thermal resistance $R_s$. Here, core is the internal body temperature $T_c$. Value of $R_s$ depends on thermal properties of skin, fat, muscles, and so forth. It should be kept in mind that this resistance is not entirely constant, even for the same patient. It may be affected by ambient and patient temperatures, patient's age, clothing, etc. In fact, this resistance value is under a constant physiological control of a patient. Temperature distribution within the probe depends on ambient temperature $T_a$, thermal insulator 10 and outer insulator 37 which is formed by a thermometer housing. Reference temperature $T_r$ is measured by second sensor 7. The two sensors permit computation of a heat flow from the patient's core to ambient via thermal resistances $R_s$, $R_r$ and $R_a$ (thermal resistance of outer insulator 37). Since resistance $R_s$ is not fixed, a true core body temperature computation is impossible. However, an approximation by a 2nd order equation can provide results with an acceptable degree of clinical accuracy. It has been shown experimentally that equation (1) is a good practical way to compute a deep body (core) temperature from temperature of skin $T_s$ and reference temperature $T_r$:

$$T_c = AT_s^2 + (B + CT_r)T_s + DT_r + E \quad (1)$$

where A, B, C, D and E are the experimentally determined constants.

It is important to note that $T_s$ is the skin temperature and not exactly what is measured by first sensor 6 that touches skin 15. The reason is that skin is a poor heat conductor and has rather low thermal capacity. Thus, touching skin 15 with plate 20 changes the skin temperature from true value of $T_s$ to some altered value $T_x$ which is actually measured by first sensor 6. Hence, before Eq. (1) can be employed, value of $T_s$ should be computed from two temperatures: temperature $T_0$ and $T_x$, where $T_0$ is temperature of first sensor 6 before it touched skin 15. The following Eq. (2) for computation of $T_s$ provides a practically sufficient accuracy for a relatively narrow ambient temperature range.

$$T_s = (T_x - T_0)\mu + T_x \quad (2)$$

where $\mu$ is an experimentally determined constant.

Figure 7:
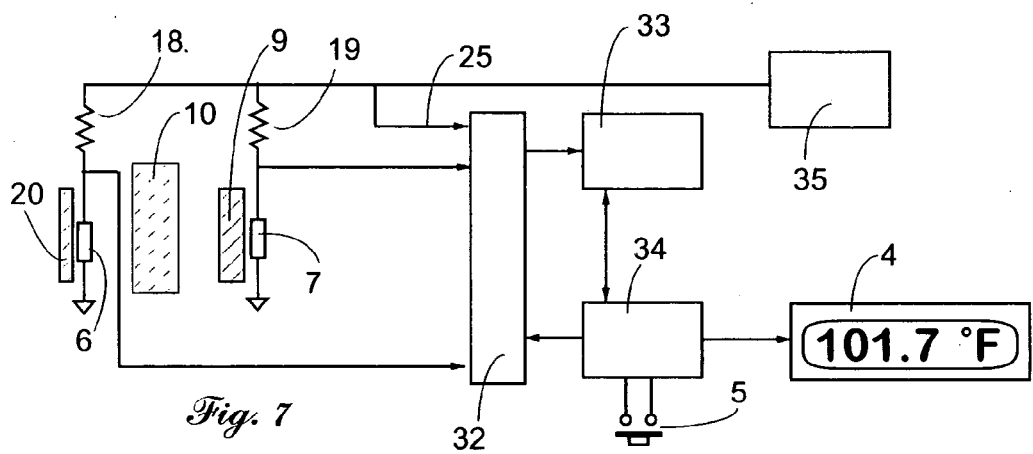
FIG. 7 is a block diagram of the thermometer

In some applications, there is no need to employ second temperature sensor to measure $T_r$ used in Eq. (1). This function may be accomplished by first temperature sensor 6 prior it comes in contact with the patient skin and preferably immediately after the device's power up. Since at that time first sensor is at housing 1 temperature, its response will be nearly the same as it would be from second sensor 7. Therefore, second sensor 7 may not be required. Thus, responses of first sensor 6 taken at different times can be used as different temperatures needed to compute the patient core temperature. Naturally, when the same sensor, that is, first sensor 6, is used for all temperature entries into Eq. (1), a number of components can be eliminated. Specifically, in that case, the following are not needed: second sensor 7, thermal insulator 10, thermal mass 9, and second pull up resistor 19 (FIG. 7).

Figure 5:
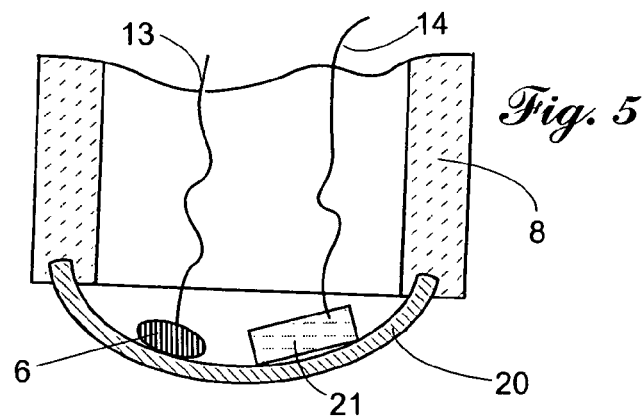
FIG. 5 represents a temperature probe with a heater.

When ambient temperatures are colder, first sensor 6 may change the skin temperature so much that it may take a much longer time to measure and compute an accurate skin temperature $T_s$ with use of Eq. (2). To speed-up the first sensor 6 response, it can be pre-warmed by an imbedded heater 21 as illustrated in FIG. 5. Heater 21, first sensor 6 and plate 20 are in an intimate thermal coupling with each other. Heater 21 and first sensor 6 are connected to the electronic circuit by conductors 14 and 13 respectively. Before the measurement, heater 21 elevates temperature of plate 20 to a level that is somewhat below an anticipated skin temperature. A good practical number for a pre-warming is 28° C. (82° F.). This pre-warmed temperature will be used in Eq. (2) as $T_0$.

Figure 6:
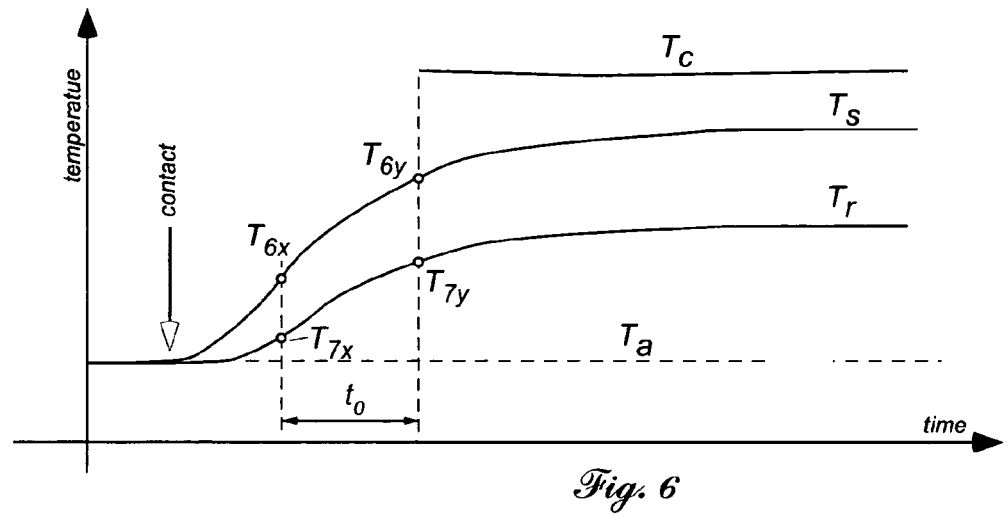
FIG. 6 shows a timing diagram of the sensor responses

FIG. 6 illustrates that both skin and reference temperatures may change in time. A predictive technique can be employed to compute a steady-state value of tempeature. This technique can be applicable to either one or both temperature sensors. It has been demonstrated in the experiment that Eq. (3) can be used to predict the finally computed temperature (either skin or reference):

$$T_s = \frac{T_{6y} - k_6 T_{6x}}{1 - k_6} \quad (3)$$

where k is an experimental constant, primarily dependent on the probe design and selected time delay $t_0$ (see FIG. 6). For the prediction, at least two reading (x and y) from each sensor should be taken with a delay $t_0$ after the sensors start moving from the ambient level $T_a$.

FIG. 7 shows a block diagram of a thermometer. Two thermistors are used as first and second sensors 6 and 7. They are pulled up by first and second pull-up resistors 18 and 19 respectively that are connected to a constant reference voltage 25 generated by power supply circuit 35. Signals from both sensors 6 and 7 are fed into multiplexer 32 which is a gate to allow passage of only one signal at a time. The multiplexer 32 output signal is applied to analog-to-digital (A/D) converter 33. All these parts are under control of microcontroller 34 which can be turned on by switch 5. The result of temperature computation is presented on display 4. It should be understood that a similar but modified circuit may be used with a probe having different types of sensors, such as thermocouples, e.g.

Figure 8:
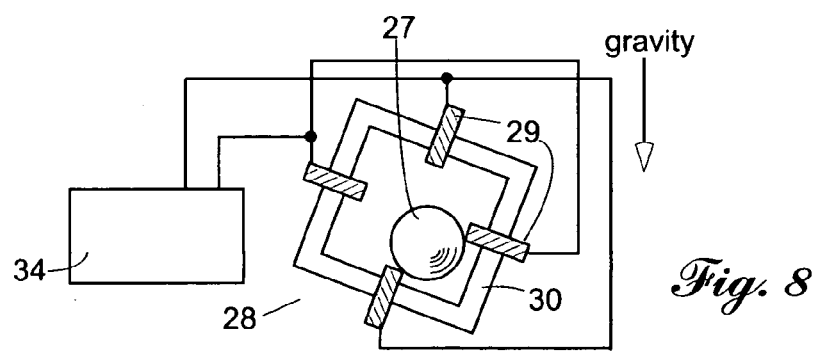
FIG. 8 is a cress-sectional view of a thermometer with a motion detector

To make the thermometer more user-friendly, some of its functions can be automated. For example, switch 5 can be eliminated entirely. Power to the circuit may be turned on automatically by a motion detector when the device is picked-up. FIG. 8 illustrates a simple motion detector 28 that is gravity operated. It has several electrodes 29 imbedded into hollow capsule 30. Electrically conductive ball 27 resides inside capsule 30. When position of the device changes after being picked up, ball 30 rolls inside capsule 30 making intermittent contacts with the internal electrodes 20. This modulates electrical resistances between the adjacent contacts and can be detected by microcontroller 34, signaling it to turn power on. Other types of motion detectors can be employed. Many of them are described in book by Jacob Fraden "Handbook of Modern Sensors" (3rd ed., Springer Verlag NY, 2004).

Figure 9:
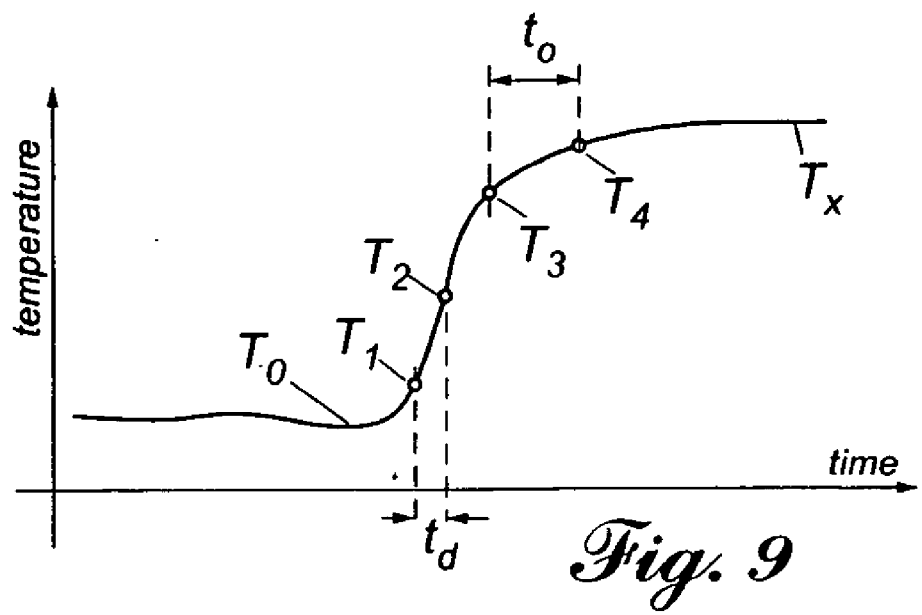
FIG. 9 is a timing diagram of the first temperature sensor response

The thermometer in this embodiment operates as follows. Initially, it is located in some storage place and its power is off. After being picked-up, motion detector 28 turns power on and temperatures from both sensors 6 and 7 are measured and computed continuously with a predetermined rate. Microcontroller constantly checks temperature changes of sensor 6 over predetermined time intervals td (FIG. 9). Temperature of first sensor 6 stays on a relatively stable level until the probe touches the patient's skin. At this moment, temperature of first sensor 6 begins to rise. A difference between temperatures $T_1$ and $T_2$ is detected to be sufficiently large and that event signals the microcontroller that the computation must begin. Temperature of first sensor 6, $T_0$ before the detection is stored and will be used for computing the skin temperature by use of Eq. (2). Predictive algorithm of Eq. (3) is applied to at least first sensor 6 or both sensors 6 and 7 and a steady state values of both sensors are computed ($T_x$ is for the first sensor). When microcontroller 34 determines that both predicted temperatures have reached sufficiently steady values, it employs Eq. (2) to compute the skin temperature Ts and subsequently uses Eq. (1) to compute the patient's core temperature $T_c$. Power is turned off automatically after a preset delay.

The invention has been described in connection with a preferred embodiment, but the invention is greater than and not intended to be limited to the particular form set forth. The invention is intended to cover such alternatives, modifications, and equivalents as may be included within the spirit and scope of the invention as defined by the appended claims.

The invention claimed is:

1. A non-invasive contact thermometer for intermittent determination of body core temperature of a patient comprising:
   a housing containing a probe;
   a guard being part of said probe;
   a first temperature sensor shielded by said guard, said guard being configured to slide within said probe and relative to said first temperature sensor after said probe is pressed against skin of the patient to bring said first temperature sensor in thermal contact with the skin;
   a thermally conductive plate attached to said first temperature sensor;
   a microcontroller for receiving an electrical signal from said first temperature sensor and for computing the body core temperature of the patient; and
   a display communicating with said microcontroller for presenting the body core temperature computed by said microcontroller.

2. A thermometer of claim 1 wherein said first temperature sensor is positioned on a movable shaft fabricated of a thermally insulating material.

3. A thermometer of claim 1 further comprising a second temperature sensor that is thermally insulated from the first temperature sensor.

4. A method of performing deep body temperature measurement from skin of a patient using a contact thermometer having a probe with a guard and a first temperature sensor shielded by the guard, the guard being movable relative to the first temperature sensor, the method comprising:
   measuring temperature of the first temperature sensor before the first temperature sensor is brought in thermal contact with the skin of the patient,
   pressing the guard against the skin to slide the guard within the probe and thereby bring the first temperature sensor in thermal contact with the skin,
   measuring temperature of the first temperature sensor after the first temperature sensor is brought in thermal contact with the skin,
   computing a deep body temperature of the patient by accounting for the temperatures measured by the first temperature sensor prior to and after contacting the skin and by experimentally determined constants, and
   displaying the deep body temperature.

5. A method of performing deep body temperature measurement of claim 4, further comprising:
   measuring temperature of the first temperature sensor at least two times after the first temperature sensor is brought in thermal contact with the skin of the patient.

6. A method of performing deep body temperature measurement of claim 4, further comprising:
   elevating the temperature of the first temperature sensor prior to pressing the guard against the skin of the patient.

7. A thermometer of claim 1, further comprising:
   a power supply communicating with said microcontroller and said first temperature sensor.

8. A thermometer of claim 1, wherein said plate is constructed from metal.

9. A thermometer of claim 1, wherein said microcontroller computes the patient's body core temperature from at least two sequential responses of said first temperature sensor.

10. A thermometer of claim 1, further comprising:
a heating element thermally coupled to said first temperature sensor.

11. A thermometer of claim 1, further comprising:
a thermally conductive sheath of a polymer material covering at least portion of said probe.

12. A method of performing deep body temperature measurement from skin of a patient using a contact thermometer having a housing, a guard extending from the housing, and a first temperature sensor shielded by the guard, the method comprising:
measuring the temperature of the housing;
pressing the guard against the skin of the patient;
moving the first temperature sensor relative to the guard to bring the first temperature sensor in thermal contact with the skin;
measuring the temperature of the first temperature sensor;
computing the deep body temperature of the patient by accounting for the temperature of the housing, the temperature measured by the first temperature sensor, and experimentally determined constants; and
displaying the deep body temperature.

13. A method of performing deep body temperature measurement of claim 12, wherein moving the first temperature sensor relative to the guard further comprises:
sliding the guard relative to the housing and the first temperature sensor.

14. A method of performing deep body temperature measurement of claim 12, wherein measuring the temperature of the housing further comprises:
measuring an initial temperature of the first temperature sensor before bringing the first temperature sensor into thermal contact with the skin, the initial temperature of the first temperature sensor approximating the temperature of the housing.

15. A method of performing deep body temperature measurement of claim 12, wherein measuring the temperature of the first temperature sensor further comprises:
measuring the temperature of the first temperature sensor at least two times after the first temperature sensor is brought in thermal contact with the skin of the patient.

16. A method of performing deep body temperature measurement of claim 12, further comprising:
elevating the temperature of the first temperature sensor prior to pressing the guard against the skin of the patient.

17. A non-invasive contact thermometer for intermittent determination of body core temperature of a patient, comprising:
a housing including a probe;
a guard being part of said probe;
a first temperature sensor shielded by said guard, said first temperature sensor being movable relative to said guard to bring said first temperature sensor in thermal contact with skin of the patient;
a thermally conductive plate attached to said first temperature sensor;
a microcontroller for receiving an electrical signal from said first temperature sensor and for computing the body core temperature of the patient; and
a display communicating with said microcontroller for presenting the body core temperature computed by said microcontroller.

18. A thermometer of claim 17, further comprising:
a sleeve extending from said housing to define a portion of said probe, said first temperature sensor extending through said sleeve.

19. A thermometer of claim 18, wherein said guard is configured to slide relative to said first temperature sensor and said sleeve after said guard is pressed against the skin of the patient to bring said first temperature sensor in thermal contact with the skin.

20. A thermometer of claim 17 wherein said first temperature sensor is positioned on a movable shaft fabricated of a thermally insulating material.

21. A thermometer of claim 17 further comprising a second temperature sensor that is thermally insulated from the first temperature sensor.

22. A method of performing deep body temperature measurement from skin of a patient using a contact thermometer having a housing, a guard extending from the housing, and a first temperature sensor shielded by the guard, the method comprising:
activating a power supply in the contact thermometer to measure the temperature of the first temperature sensor, the power supply communicating with a microcontroller that receives electrical signals from the first temperature sensor;
pressing the guard against the skin of the patient;
moving the first temperature sensor relative to the guard to bring the first temperature sensor in thermal contact with the skin, wherein the microcontroller receives electrical signals corresponding to the temperatures measured by the first temperature sensor after the first temperature sensor is placed in thermal contact with the skin;
viewing a deep body temperature of the patient on a display communicating with the microcontroller, wherein the microcontroller computes the deep body temperature by accounting for the temperatures measured by the first temperature sensor after contacting the skin and by experimentally determined constants.

23. A method of performing deep body temperature measurement of claim 22, wherein activating the power supply further comprises:
activating a switch on the housing, the switch communicating with the microcontroller.

* * * * *